(12) United States Patent
Kim (10) Patent No.: US 11,932,139 B2
(45) Date of Patent: Mar. 19, 2024

(54) DEVICE AND METHOD FOR CONTROLLING VEHICLE

(71) Applicants: HYUNDAI MOTOR COMPANY, Seoul (KR); KIA CORPORATION, Seoul (KR)

(72) Inventor: Gyun Ha Kim, Incheon (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 413 days.

(21) Appl. No.: 17/333,440

(22) Filed: May 28, 2021

(65) Prior Publication Data
US 2022/0169152 A1 Jun. 2, 2022

(30) Foreign Application Priority Data
Dec. 2, 2020 (KR) ........................ 10-2020-0166905

(51) Int. Cl.
*B60N 2/02* (2006.01)
*B60N 2/06* (2006.01)
*B60N 2/20* (2006.01)
*G01C 3/08* (2006.01)
*G01N 33/497* (2006.01)
*G01S 13/08* (2006.01)

(52) U.S. Cl.
CPC ....... *B60N 2/0244* (2013.01); *G01N 33/4972* (2013.01); *B60N 2/0268* (2023.08); *B60N 2/06* (2013.01); *B60N 2/20* (2013.01); *G01C 3/08* (2013.01); *G01S 13/08* (2013.01)

(58) Field of Classification Search
CPC .......... B60N 2/0244; B60N 2/06; B60N 2/20; B60N 2/0268; G01N 33/4972; G01C 3/08
USPC ........................................................ 701/49
See application file for complete search history.

(56) References Cited

U.S. PATENT DOCUMENTS

| | | | | |
|---|---|---|---|---|
| 5,531,225 A | * | 7/1996 | Nawata | G01N 33/4972 340/576 |
| 8,183,527 B2 | * | 5/2012 | Taguchi | G01N 21/3504 250/338.5 |
| 11,747,441 B2 | * | 9/2023 | Shirahatti | G01S 13/08 342/61 |
| 2008/0142713 A1 | * | 6/2008 | Breed | B60R 21/01526 250/330 |
| 2008/0157510 A1 | * | 7/2008 | Breed | E05F 15/43 701/45 |
| 2008/0292146 A1 | * | 11/2008 | Breed | B60N 2/002 382/118 |

(Continued)

*Primary Examiner* — Yazan A Soofi
(74) *Attorney, Agent, or Firm* — MCDONNELL BOEHNEN HULBERT & BERGHOFF LLP (57) ABSTRACT

A device for controlling a vehicle includes a first sensor that senses boarding of a driver, a second sensor that senses alcohol contained in exhalation of the driver, and a controller that sets a location of a seat such that a distance from the second sensor to the driver becomes a predetermined distance. The vehicle control device may control the seat location such that a distance between the driver and a sensing device is maintained to be equal to or less than the predetermined distance when measuring the alcohol to allow the alcoholic ingredient of the driver to be accurately measured, and may arouse awareness of the driver of the alcohol measurement as the seat location is controlled.

18 Claims, 8 Drawing Sheets

(56) References Cited

U.S. PATENT DOCUMENTS

2009/0090577 A1* 4/2009 Takahashi .......... G01N 33/4972
340/576
2017/0305349 A1* 10/2017 Naboulsi ................ B60R 1/025
2018/0079278 A1* 3/2018 Kirpichnikov ..... B60H 1/00742
2021/0338146 A1* 11/2021 Pham .................. A61B 5/0205

* cited by examiner

| | SETTING A | SETTING B | SETTING C |
|---|---|---|---|
| HEIGHT | 155~165cm | 165~175cm | 175~185cm |
| SEAT REFERENCE LOCATION COORDINATES | $X_{STANDARDH}-50mm$, $Y_{STANDARDH}$, $Z_{STANDARDH}$ | $X_{STANDARDH}$, $Y_{STANDARDH}$, $Z_{STANDARDH}$ | $X_{STANDARDH}+50mm$, $Y_{STANDARDH}$, $Z_{STANDARDH}$ |
| DRIVER REFERENCE LOCATION COORDINATES | $X_{STANDARDV}-50mm$, $Y_{STANDARDV}$, $Z_{STANDARDV}-50mm$ | $X_{STANDARDV}$, $Y_{STANDARDV}$, $Z_{STANDARDV}$ | $X_{STANDARDV}+50mm$, $Y_{STANDARDV}$, $Z_{STANDARDV}+50mm$ |

DEVICE AND METHOD FOR CONTROLLING VEHICLE

CROSS REFERENCE TO RELATED APPLICATIONS

This application claims the benefit of priority to Korean Patent Application No. 10-2020-0166905, filed in the Korean Intellectual Property Office on Dec. 2, 2020, the entire contents of which are incorporated herein by reference.

TECHNICAL FIELD

The present disclosure relates to a device and a method for controlling a vehicle.

BACKGROUND

Recently, a technology for measuring an alcoholic ingredient in exhalation of a driver and limiting travel of a vehicle when the alcohol is detected has been developed to prevent drunk driving of the driver. Currently, schemes for measuring the alcoholic ingredient of the driver may include an electrochemical scheme using a mouthpiece and an optical scheme not using the mouthpiece. The driver must exhale into a sensing device at least once to measure the alcoholic ingredient.

In particular, for accurate alcoholic ingredient measurement, the driver must exhale within a predetermined distance from the sensing device, but a case in which the driver and the sensing device do not maintain a predetermined distance occurs depending on a location of a seat preferred by the driver. In this case, because the driver needs to move the seat to maintain the predetermined distance, there is a limit that causes inconvenience to the driver.

SUMMARY

The present disclosure has been made to solve the above-mentioned problems occurring in the prior art while advantages achieved by the prior art are maintained intact.

An aspect of the present disclosure provides a device and a method for controlling a vehicle that maintain a predetermined distance from an alcohol sensing device when measuring alcohol of a driver.

The technical problems to be solved by the present inventive concept are not limited to the aforementioned problems, and any other technical problems not mentioned herein will be clearly understood from the following description by those skilled in the art to which the present disclosure pertains.

According to an aspect of the present disclosure, a device for controlling a vehicle includes a first sensor that senses boarding of a driver, a second sensor that senses alcohol contained in exhalation of the driver, and a controller that sets a location of a seat such that a distance from the second sensor to the driver becomes a predetermined distance.

In one implementation, the controller may generate reference location coordinates of the driver and reference location coordinates of the seat in advance.

In one implementation, the controller may adjust the reference location coordinates of the driver and the reference location coordinates of the seat based on information of the driver.

In one implementation, the controller may set the location of the seat such that a location of the driver corresponds to the reference location coordinates of the driver and the location of the seat corresponds to the reference location coordinates of the seat.

In one implementation, the device may further include at least one of a camera and/or a radar for sensing a face of the driver.

In one implementation, the controller may calculate a distance from the face of the driver to the second sensor.

In one implementation, the controller may set the location of the seat based on the distance from the face of the driver to the second sensor.

In one implementation, the controller may control an angle of the seat and a sliding operation of the seat based on the set location of the seat.

In one implementation, the controller may determine whether a carbon dioxide concentration contained in the exhalation of the driver less than or equal to a reference value.

In one implementation, the controller may control an angle of the seat and a sliding operation of the seat such that the distance from the second sensor to the driver becomes less than the predetermined distance when the carbon dioxide concentration is less than or equal to the reference value.

According to another aspect of the present disclosure, a method for controlling a vehicle includes sensing boarding of a driver, and setting a location of a seat such that a distance from a sensor for sensing alcohol contained in exhalation of the driver to the driver becomes a predetermined distance.

In one implementation, the method may further include generating reference location coordinates of the driver and reference location coordinates of the seat in advance.

In one implementation, the method may further include adjusting the reference location coordinates of the driver and the reference location coordinates of the seat based on information of the driver.

In one implementation, the setting of the location of the seat may include setting the location of the seat such that a location of the driver corresponds to the reference location coordinates of the driver and the location of the seat corresponds to the reference location coordinates of the seat.

In one implementation, the method may further include sensing a face of the driver using at least one of a camera and/or a radar.

In one implementation, the method may further include calculating a distance from the face of the driver to the sensor.

In one implementation, the location of the seat may be set based on the distance from the face of the driver to the sensor.

In one implementation, the method may further include controlling an angle of the seat and a sliding operation of the seat based on the set location of the seat.

In one implementation, the method may further include determining whether a carbon dioxide concentration contained in the exhalation of the driver exceeds a reference value.

In one implementation, the method may further include controlling an angle of the seat and a sliding operation of the seat such that the distance from the sensor to the driver becomes less than the predetermined distance when the carbon dioxide concentration is less than or equal to the reference value.

BRIEF DESCRIPTION OF THE FIGURES

The above and other objects, features and advantages of the present disclosure will be more apparent from the following detailed description taken in conjunction with the accompanying drawings.

DETAILED DESCRIPTION

Hereinafter, some embodiments of the present disclosure will be described in detail with reference to the exemplary drawings. In adding the reference numerals to the components of each drawing, it should be noted that the identical or equivalent component is designated by the identical numeral even when they are displayed on other drawings. Further, in describing the embodiment of the present disclosure, a detailed description of the related known configuration or function will be omitted when it is determined that it interferes with the understanding of the embodiment of the present disclosure.

In describing the components of the embodiment according to the present disclosure, terms such as first, second, A, B, (a), (b), and the like may be used. These terms are merely intended to distinguish the components from other components, and the terms do not limit the nature, order or sequence of the components. Unless otherwise defined, all terms including technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
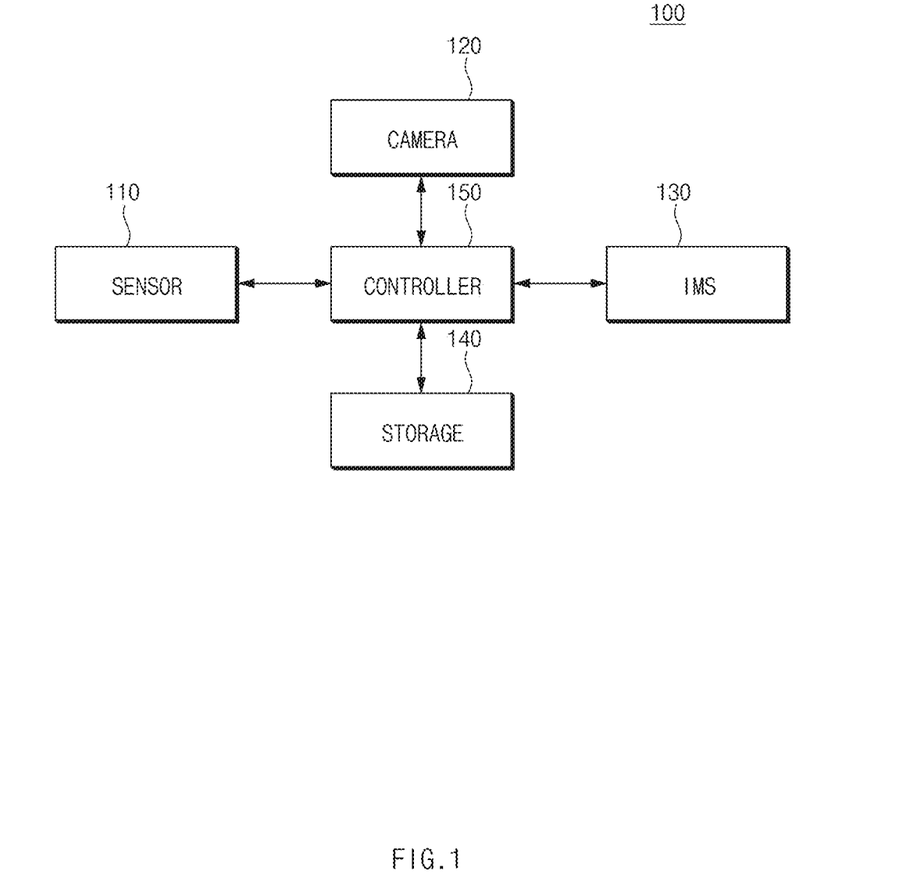
FIG. 1 is a view illustrating a configuration of a vehicle control device according to an embodiment of the present disclosure.

FIG. 1 is a view illustrating a configuration of a vehicle control device according to an embodiment of the present disclosure.

As shown in FIG. 1, a vehicle control device 100 according to an embodiment of the present disclosure may include a sensor 110, a camera 120, an integrated memory system (IMS) 130, storage 140, and a controller 150.

Figure 2:
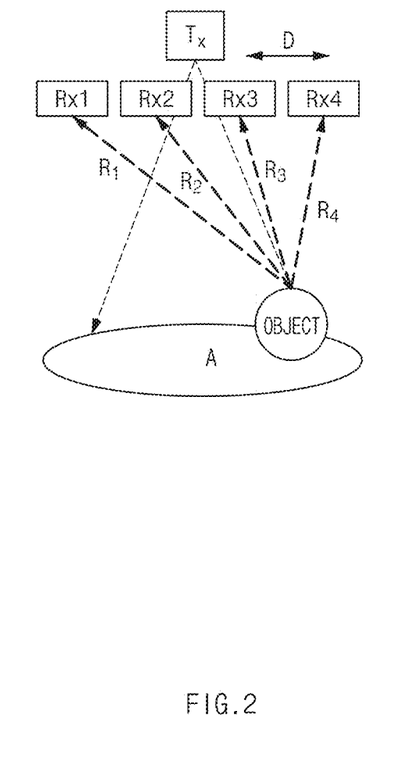
FIG. 2 is a diagram schematically illustrating a scheme for calculating coordinates of an object according to an embodiment of the present disclosure.
Figure 3A:
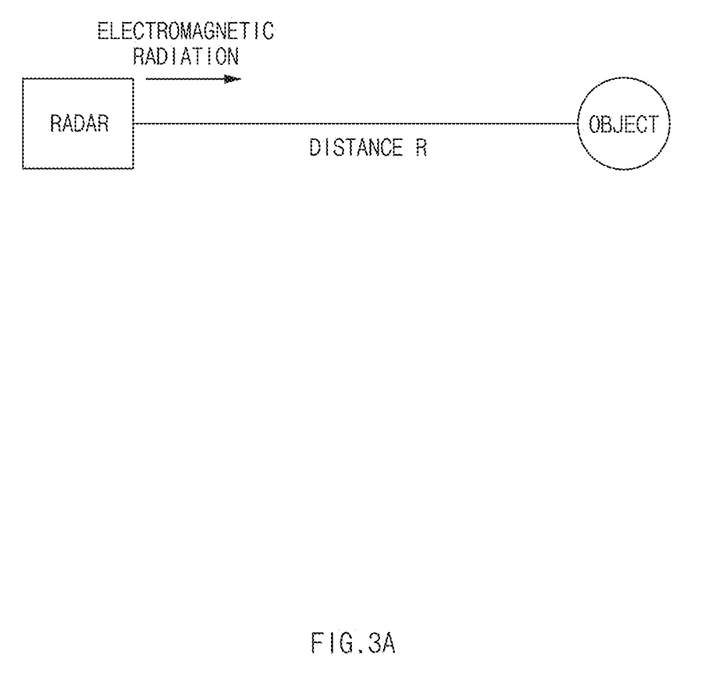
FIG. 3A is a diagram illustrating a case in which a distance between a FMCW radar and an object is R.
Figure 3B:
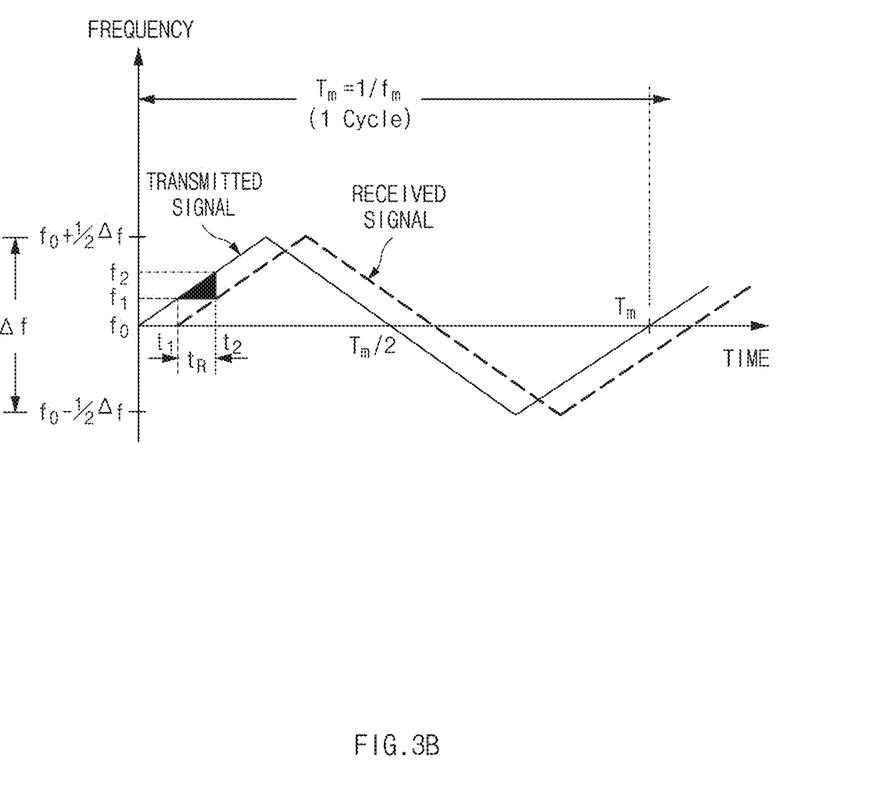
FIG. 3B is a graph illustrating a change in a frequency of a radar for calculating R.

The sensor 110 may include a plurality of sensors, such as a seat sensor, an alcohol sensor, a door sensor, and a distance sensor. The seat sensor may sense sitting of a driver. The controller 150 may determine whether the driver is sitting based on the information sensed by the seat sensor. The alcohol sensor may measure an alcohol content contained in exhalation of the driver, and may measure a carbon dioxide concentration contained in the exhalation of the driver. The door sensor may sense opening or closing of a door. In addition, the distance sensor may sense the driver. According to an embodiment, the distance sensor may include a radar. As an example, the radar may include a frequency modulated continuous wave (FMCW) radar, an impulse-radio ultra wideband (IR-UWB) radar, a continuous wave (CW) radar, and the like. The FMCW radar may obtain information on a time it takes to return after an electromagnetic wave is radiated by a difference in a frequency of the electromagnetic wave reflected from an object by changing the frequency of the electromagnetic wave linearly with time. The FMCW radar may calculate a location (face coordinates) of the driver based on the obtained time information and a speed of the electromagnetic wave (a speed of light), and calculate a distance from the alcohol sensor to the driver (the face of the driver). FIGS. 2 and 3 will be referred for a more detailed description. FIG. 2 is a diagram schematically illustrating a scheme for calculating coordinates of an object according to an embodiment of the present disclosure.

As shown in FIG. 2, in the FMCW radar, a transmitter $T_x$ radiates the electromagnetic wave to a preset region "A". When it is sensed by a plurality of receivers Rx1, Rx2, Rx3, and Rx4 that an object exists in the preset region "A", the FMCW radar may calculate coordinates of the object using distances R1, R2, R3, and R4 from the object to the respective plurality of receivers and a distance "D" between the plurality of receivers.

When calculating the face coordinates of the driver using the scheme shown in FIG. 2, the FMCW radar may calculate the distance from the face coordinates of the driver to the alcohol sensor based on FIG. 3A and FIG. 3B.

FIG. 3A is a diagram illustrating a case in which a distance between a FMCW radar and an object is R, and FIG. 3B is a graph illustrating a change in a frequency of a radar for calculating R.

As shown in FIG. 3A and FIG. 3B, when the electromagnetic wave having a frequency $f_1$ radiated at a time point $t_1$ from the transmitter reaches the receiver at a time point $t_2$, and when a time the electronic wave radiated from the transmitter returns to the receiver is $t_R(=t_2-t_1)$, the FMCW radar may calculate $t_R$ using Calculation Equation 1.

$$t_R = 2*R/c \qquad \text{Calculation Equation 1:}$$

where c is the speed of the light.

The FMCW radar may calculate a difference between transmission/reception frequencies at the time point $t_2$ as $f_R(=f_2-f_1)$, and calculate a frequency change rate during a time $T_m$ using calculation Equation 2.

$$F_C = 2*\Delta f/T_m \qquad \text{Calculation Equation 2:}$$

The FMCW radar may rearrange Calculation Equation 2 to Calculation Equation 3 using a modulation rate ($f_m=1/T_m$) of the frequency based on a relationship (f=1/T) between the frequency and a period.

$$F_C = 2*\Delta f * f_m = (f_2-f_1)t_R = f_R/T_R \qquad \text{Calculation Equation 3:}$$

The FMCW radar may calculate the distance R by substituting Calculation Equation 1 into Calculation Equation 3 to derive Calculation Equation 4.

$$R = cf_R/(4\Delta f * f_m) \qquad \text{Calculation Equation 4:}$$

The camera 120 may sense the driver. According to an embodiment of the present disclosure, the camera 120 may sense the face of the driver and may calculate a distance between the camera 120 and the face of the driver. According to an embodiment, the camera 120 may include a cluster time of flight (ToF) camera attached to a cluster. For reference, the cluster ToF camera may calculate a distance from the camera to a target object using a time it takes for an infrared beam emitted to the target object to be reflected from the target object and return. In addition, the camera 120 may be disposed on one side of a pillar, which is a pole connecting a vehicle body and a roof with each other, to sense the driver before the boarding. According to an embodiment, the camera 120 may be disposed on a B-pillar located at a center of a front door and a rear door of the vehicle.

The integrated memory system (IMS) 130 may include a device that stores an optimal driving location suitable for the driver and automatically adjusts a driving posture based on the stored driving location when the driver boards.

The storage 140 may store at least one algorithm that performs operation or execution of various commands for an operation of the vehicle control device according to an embodiment of the present disclosure. The storage 140 may include at least one storage medium of a flash memory, a hard disc, a memory card, a read-only memory (ROM), a random access memory (RAM), an electrically erasable programmable read-only memory (EEPROM), a programmable read-only memory (PROM), a magnetic memory, a magnetic disk, and/or an optical disk. According to an embodiment of the present disclosure, the controller 150 may store a predetermined distance capable of accurately measuring the alcohol contained in the exhalation of the driver, and store driver reference location coordinates and seat location coordinates set according to an embodiment.

The controller 150 may be implemented by various processing devices such as a microprocessor or the like with an embedded semiconductor chip or the like capable of performing the operation or the execution of the various commands, and may control overall operations of the vehicle control device according to an embodiment of the present disclosure. According to an embodiment, the controller 150 may set a seat location such that the distance from the alcohol sensor to the driver becomes a predetermined distance.

The controller 150 may first generate and store the reference location coordinates of the driver and reference location coordinates of the seat. In this connection, the reference location coordinates of the driver may be generated based on a location of a philtrum of the driver that may comply with visibility in a forward direction of the vehicle (a range of vision of the driver). The reference location coordinates of the driver may be generated differently based on a seat angle. In addition, the reference location coordinates of the seat may be generated based on a Hyundai reference sitting point (HRSP) based on a height of the driver for upper 95%.

Figure 4:
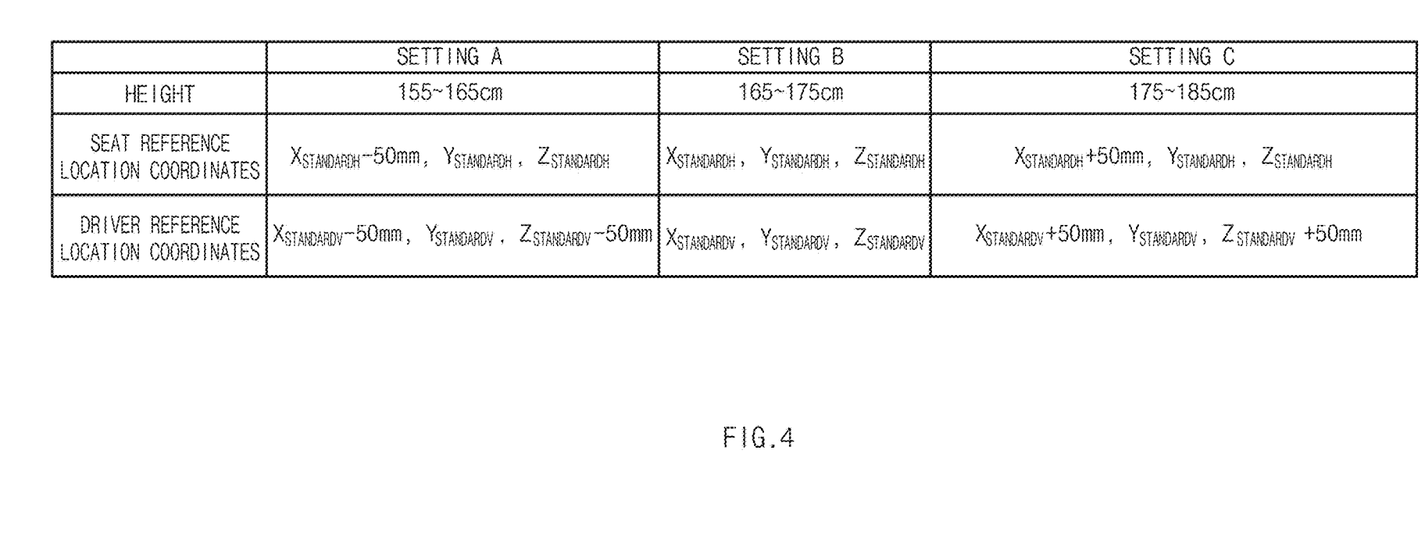
FIG. 4 is a diagram illustrating reference location coordinates of a driver and reference location coordinates of a seat set according to an embodiment of the present disclosure.

In addition, the controller 150 may adjust the reference location coordinates of the driver and the reference location coordinates of the seat based on driver information. According to an embodiment, the controller 150 may infer the height based on the driver sensed by the camera (the camera disposed on the B-pillar), and adjust the reference location coordinates of the driver and the reference location coordinates of the seat based on the height of the driver. FIG. 4 will be referred for a more detailed description.

FIG. 4 is a diagram illustrating reference location coordinates of a driver and reference location coordinates of a seat set according to an embodiment of the present disclosure.

As shown in FIG. 4, when reference location coordinates $(X_{standardV}, Y_{standardV}, Z_{standardV})$ of the driver and reference location coordinates $(X_{standardH}, Y_{standardH}, Z_{standardH})$ of the seat generated based on the height (e.g., 165 to 175 cm) of the driver of the upper 95% are set as setting B, the controller 150 may adjust the reference location coordinates of the driver to $(X_{standardV}-50 \text{ mm}, Y_{standardV}, Z_{standardV}-50 \text{ mm})$ and the reference location coordinates of the seat to $(X_{standardH}-50 \text{ mm}, Y_{standardV}, Z_{standardV})$ and set the adjusted coordinates as setting A when the height of the driver is in a range between 155 and 165 cm. In addition, when the height of the driver is in a range between 175 and 185 cm, the reference location coordinates of the driver are adjusted to $(X_{standardV}+50 \text{ mm}, Y_{standardV}, Z_{standardV}+50 \text{ mm})$, and the reference location coordinates of the seat may be adjusted to $(X_{standardH}+50 \text{ mm}, Y_{standardV}, Z_{standardV})$.

Figure 5:
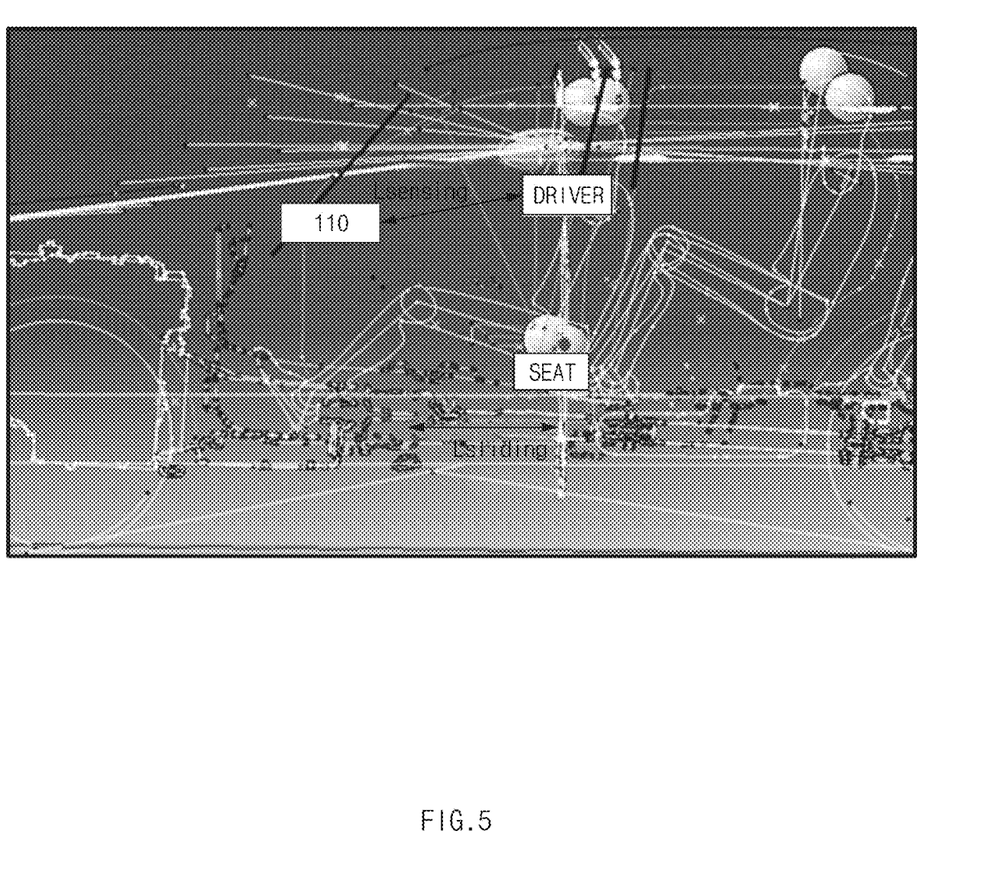
FIG. 5 is a schematic view illustrating a vehicle control device according to an embodiment of the present disclosure.

When it is determined that the door is in an open (unlocked) state, the controller 150 may determine whether the driver is sitting in the seat after the door is opened, or whether an ignition is turned on. When it is determined that the driver is sitting in the seat or the ignition is turned on, the controller 150 may set the seat location such that the distance from the alcohol sensor to the driver becomes the predetermined distance. According to an embodiment of the present disclosure, the predetermined distance may be in a range between 350 mm and 450 mm. FIG. 5 will be referred for a more detailed description.

FIG. 5 is a schematic view illustrating a vehicle control device according to an embodiment of the present disclosure.

According to an embodiment, as shown in FIG. 3, the controller 150 may set the seat location such that the location of the driver corresponds to the reference location coordinates of the driver generated in advance or the location of the seat corresponds to the reference location coordinates of the seat generated in advance for a distance (Lsensing) from the alcohol sensor 110 to the driver to become the predetermined distance. To this end, the controller 150 may control a sliding operation (in a front and rear direction) of the seat to adjust a length Lsliding or control the angle of the seat.

According to another embodiment, the controller 150 may control the sliding operation (in the front and rear direction) of the seat such that the distance from the alcohol sensor to the driver obtained from the camera 120 and the FMCW radar becomes the predetermined distance, thereby adjusting the length Lsliding or control the angle of the seat.

When the exhalation of the driver is introduced, the controller 150 may start measuring the alcohol in the exhalation of the driver. In addition, the controller 150 may also measure the carbon dioxide concentration in the exhalation of the driver.

The controller 150 may determine whether the carbon dioxide concentration in the exhalation of the driver exceeds a reference value. When the carbon dioxide concentration in the exhalation of the driver exceeds the reference value, the controller 150 may determine that the exhalation of the driver has been accurately introduced. When it is determined that the exhalation of the driver has been accurately introduced, the controller 150 may calculate a blood alcohol content.

On the other hand, when the carbon dioxide concentration in the exhalation of the driver does not exceed the reference value, the controller 150 may set the seat location such that the distance from the alcohol sensor to the driver (the driver face) becomes smaller than the predetermined distance. According to an embodiment, the controller 150 may set the seat location at which the distance from the alcohol sensor to the driver (the driver face) obtained by the camera becomes smaller than the predetermined distance, and control the sliding operation of the seat (in the front and rear directions) or control the angle of the seat.

Figure 6:
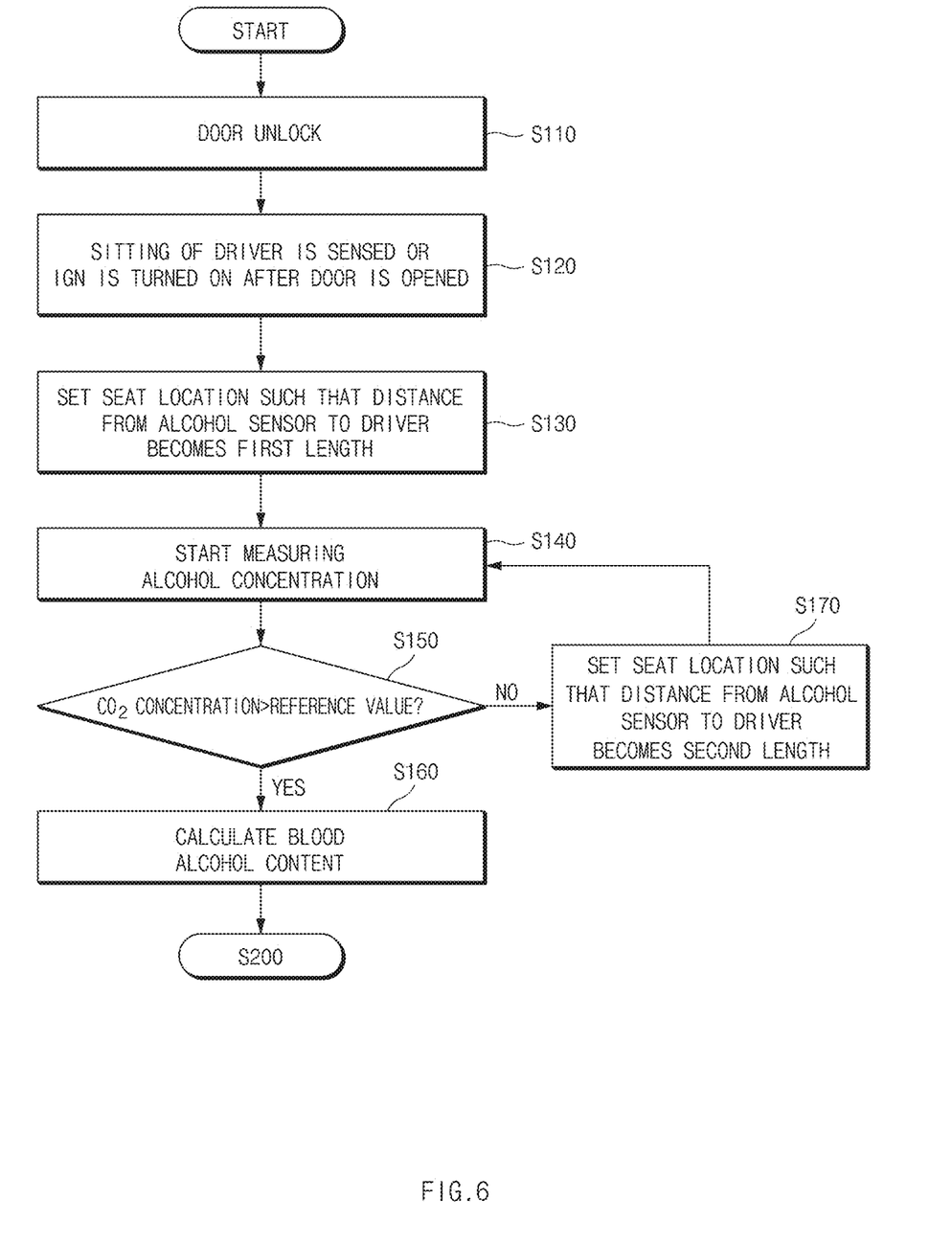
FIG. 6 is a flowchart illustrating a vehicle control method according to an embodiment of the present disclosure.

FIG. 6 is a flowchart illustrating a vehicle control method according to an embodiment of the present disclosure.

As shown in FIG. 6, when it is determined that the door is in the open (unlocked) state at S110, the controller 150 may determine whether the driver is sitting in the seat after the door is opened, or whether the ignition is turned on.

When it is determined that the driver is sitting in the seat or the ignition is turned on after the door is opened at S120, the controller 150 may set the seat location such that the distance from the alcohol sensor to the driver becomes the predetermined distance (a first length) at S130. According to an embodiment, the predetermined distance may be in the range between 350 mm and 450 mm.

According to an embodiment, in S130, the controller 150 may set the seat location such that the location of the driver corresponds to the reference location coordinates of the driver generated in advance or the location of the seat corresponds to the reference location coordinates of the seat generated in advance for the distance (Lsensing) from the alcohol sensor 110 to the driver to become the predetermined distance. To this end, the controller 150 may control the sliding operation (in the front and rear direction) of the seat or control the angle of the seat.

Further, according to another embodiment, in S130, the controller 150 may control the sliding operation of the seat or control the angle of the seat such that the distance from the alcohol sensor to the driver obtained from the camera 120 becomes the predetermined distance.

When the exhalation of the driver is introduced, the controller 150 may start measuring the alcohol in the exhalation of the driver at S140. The controller 150 may measure the carbon dioxide concentration in the exhalation of the driver, and may determine whether the carbon dioxide concentration exceeds the reference value at S150.

When it is determined in S150 that the carbon dioxide concentration in the exhalation of the driver exceeds the reference value (Y), the controller 150 may determine that the exhalation of the driver has been accurately introduced. When it is determined that the exhalation of the driver has been accurately introduced, the controller 150 may calculate the blood alcohol content at S160.

On the other hand, when it is determined that the carbon dioxide concentration in the exhalation of the driver does not exceed the reference value (N), the controller 150 may set the seat location such that the distance from the alcohol sensor to the driver (the driver face) becomes (a second length) smaller than the predetermined distance at S170. According to an embodiment, in S170, the controller 150 may set the seat location at which the distance from the alcohol sensor to the driver (the driver face) obtained by the camera or the FMCW radar becomes smaller than the predetermined distance, and control the sliding operation of the seat or control the angle of the seat. When the seat location is reset in S170, S140 may be performed.

Figure 7:
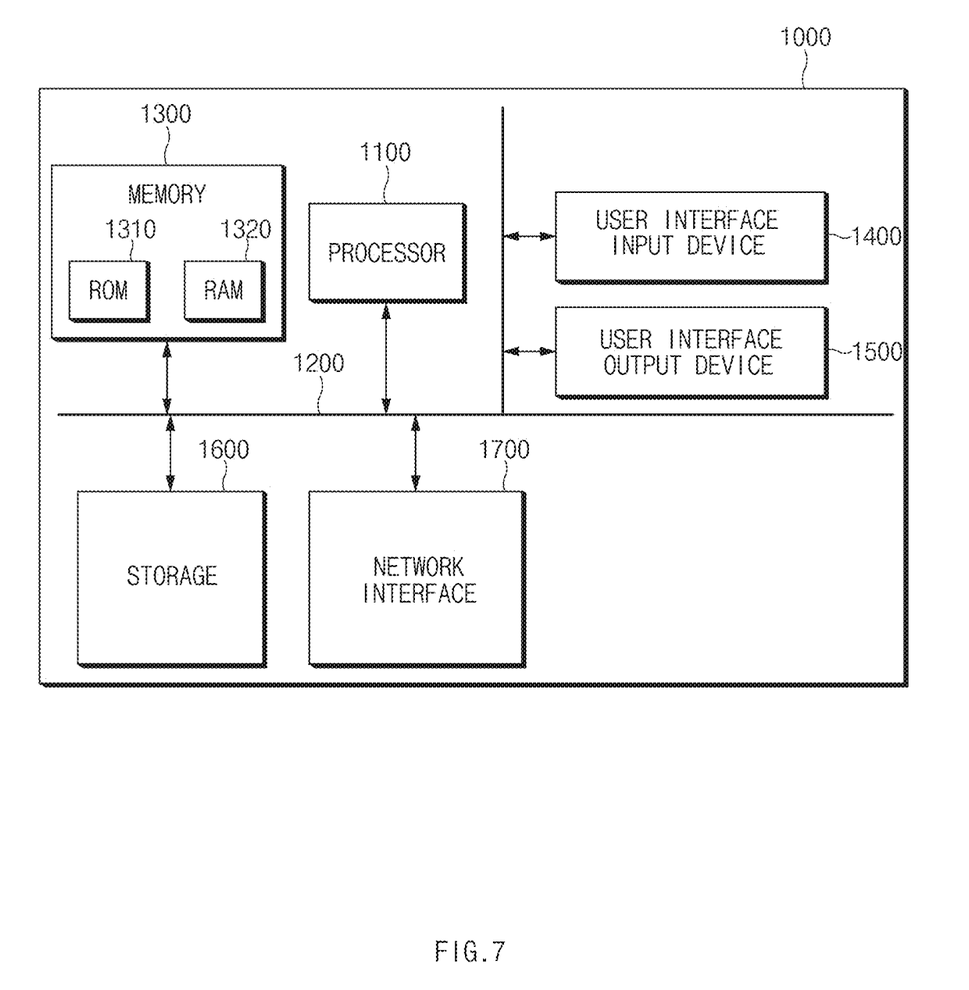
FIG. 7 is a diagram illustrating a configuration of a computing system executing a method according to an embodiment of the present disclosure.

FIG. 7 is a diagram illustrating a configuration of a computing system executing a method according to an embodiment of the present disclosure.

Referring to FIG. 7, a computing system 1000 may include at least one processor 1100, a memory 1300, a user interface input device 1400, a user interface output device 1500, storage 1600, and a network interface 1700 connected via a bus 1200.

The processor 1100 may be a central processing unit (CPU) or a semiconductor device that performs processing on commands stored in the memory 1300 and/or the storage 1600. The memory 1300 and the storage 1600 may include various types of volatile or non-volatile storage media. For example, the memory 1300 may include a ROM (Read Only Memory) 1310 and a RAM (Random Access Memory) 1320.

Thus, the operations of the method or the algorithm described in connection with the embodiments disclosed herein may be embodied directly in hardware or a software module executed by the processor 1100, or in a combination thereof. The software module may reside on a storage medium (that is, the memory 1300 and/or the storage 1600) such as a RAM, a flash memory, a ROM, an EPROM, an EEPROM, a register, a hard disk, a removable disk, and a CD-ROM. The exemplary storage medium is coupled to the processor 1100, which may read information from, and write information to, the storage medium. In another method, the storage medium may be integral with the processor 1100. The processor and the storage medium may reside within an application specific integrated circuit (ASIC). The ASIC may reside within the user terminal. In another method, the processor and the storage medium may reside as individual components in the user terminal.

The description above is merely illustrative of the technical idea of the present disclosure, and various modifications and changes may be made by those skilled in the art without departing from the essential characteristics of the present disclosure.

Therefore, the embodiments disclosed in the present disclosure are not intended to limit the technical idea of the present disclosure but to illustrate the present disclosure, and the scope of the technical idea of the present disclosure is not limited by the embodiments. The scope of the present disclosure should be construed as being covered by the scope of the appended claims, and all technical ideas falling within the scope of the claims should be construed as being included in the scope of the present disclosure.

The vehicle control device according to an embodiment of the present disclosure may control the seat location such that the distance between the driver and the sensing device is maintained to be equal to or less than the predetermined distance when measuring the alcohol to allow the alcoholic ingredient of the driver to be accurately measured, and may arouse awareness of the driver of the alcohol measurement as the seat location is controlled.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

The invention claimed is:

1. A device for controlling a vehicle, the device comprising:
   a first sensor configured to sense boarding of a driver;
   a second sensor configured to sense alcohol contained in exhalation of the driver; and
   a controller configured to set a location of a seat such that a distance from the second sensor to the driver becomes a predetermined distance;
   wherein the controller is configured to determine whether a carbon dioxide concentration contained in the exhalation of the driver exceeds a reference value, and reset the location of the seat based on the determination result.

2. The device of claim 1, wherein the controller is configured to generate reference location coordinates of the driver and reference location coordinates of the seat in advance of setting the location of the seat.

3. The device of claim 2, wherein the controller is configured to adjust the reference location coordinates of the driver and the reference location coordinates of the seat based on information of the driver.

4. The device of claim 2, wherein the controller is configured to set the location of the seat such that a location of the driver corresponds to the reference location coordinates of the driver, and the location of the seat corresponds to the reference location coordinates of the seat.

5. The device of claim 1, further comprising:
at least one of a camera or a radar for sensing a face of the driver.

6. The device of claim 5, wherein the controller is configured to calculate a distance from the face of the driver to the second sensor.

7. The device of claim 6, wherein the controller is configured to set the location of the seat based on the distance from the face of the driver to the second sensor.

8. The device of claim 1, wherein the controller is configured to control an angle of the seat and a sliding operation of the seat based on the set location of the seat.

9. The device of claim 1, wherein the controller is configured to control an angle of the seat and a sliding operation of the seat such that the distance from the second sensor to the driver becomes less than the predetermined distance when the carbon dioxide concentration is less than or equal to the reference value.

10. A method for controlling a vehicle, the method comprising:
sensing boarding of a driver by a first sensor; and
setting a location of a seat by a controller, such that a distance from a sensor for sensing alcohol contained in exhalation of the driver to the driver becomes a predetermined distance;
wherein the controller is configured to determine whether a carbon dioxide concentration contained in the exhalation of the driver exceeds a reference value, and reset the location of the seat based on the determination result.

11. The method of claim 10, further comprising:
generating reference location coordinates of the driver and reference location coordinates of the seat in advance of setting the location of the seat.

12. The method of claim 11, further comprising:
adjusting the reference location coordinates of the driver and the reference location coordinates of the seat based on information of the driver.

13. The method of claim 11, wherein the setting of the location of the seat includes:
setting the location of the seat such that a location of the driver corresponds to the reference location coordinates of the driver and the location of the seat corresponds to the reference location coordinates of the seat.

14. The method of claim 10, further comprising:
sensing a face of the driver using at least one of a camera or a radar.

15. The method of claim 14, further comprising:
calculating a distance from the face of the driver to the sensor.

16. The method of claim 15, wherein the location of the seat is set based on the distance from the face of the driver to the sensor.

17. The method of claim 10, further comprising:
controlling an angle of the seat and a sliding operation of the seat based on the set location of the seat.

18. The method of claim 10, further comprising:
controlling an angle of the seat and a sliding operation of the seat such that the distance from the sensor to the driver becomes less than the predetermined distance when the carbon dioxide concentration is less than or equal to the reference value.

* * * * *